United States Patent [19]

Atwal

[11] Patent Number: 4,859,676
[45] Date of Patent: Aug. 22, 1989

[54] 2-OXO-1-SULFONYL PYRAZOLO(1,5-A) PYRIMIDINE-6-CARBOXYLIC ACID ESTERS

[75] Inventor: Karnail Atwal, Cranbury, N.J.

[73] Assignee: E. R. Squibb & Sons, Inc., Princeton, N.J.

[21] Appl. No.: 145,004

[22] Filed: Jan. 19, 1988

[51] Int. Cl.$^4$ ............................................. C07D 487/04
[52] U.S. Cl. .................................... 514/258; 544/281; 544/279; 544/278
[58] Field of Search ....................... 544/281, 279, 278; 514/258

[56] References Cited

U.S. PATENT DOCUMENTS 2,593,890  4/1952  Kellog ................................. 544/281
4,746,656  5/1988  Atwal ................................. 544/281

FOREIGN PATENT DOCUMENTS 0163240  12/1985  European Pat. Off. .
599891   3/1948   United Kingdom .

OTHER PUBLICATIONS

Allen et al., "The Structure of Certain Polyazaindenes. I. Absorption Spectra", J. Org. Chem. 24, 779–787 (1959).

Primary Examiner—Mukund J. Shah
Assistant Examiner—C. L. Cseh
Attorney, Agent, or Firm—Theodore R. Furman, Jr.

[57] ABSTRACT

Cardiovascular activity is exhibited by compounds having the formula

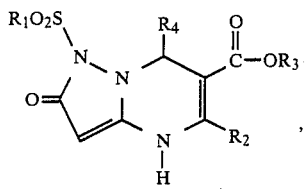

or a pharmaceutically acceptable salt thereof wherein
$R_1$ is alkyl, cycloalkyl, aryl, $-(CH_2)_n-Y_1$, or halo substituted alkyl;
$R_2$ is hydrogen, alkyl, alkenyl, alkynyl, cycloalkyl, aryl, $-(CH_2)_n-Y_1$, or halo substituted alkyl;
$R_3$ is hydrogen, alkyl, cycloalkyl, aryl, $-(CH_2)_n-Y_2$, $-(CH_2)_p-Y_3$, or halo substituted alkyl;
$R_4$ is aryl;
$Y_1$ is cycloalkyl, aryl, hydroxyl, alkoxy, aryl$-(CH_2)_m-O-$, mercapto, alkylthio, aryl$-(CH_2)_m-S-$, amino substituted amino, carbamoyl, (substituted amino)

$$\text{(substituted amino)} - \overset{O}{\underset{\|}{C}} -, \text{ carboxyl, alkoxycarbonyl, alkyl} - \overset{O}{\underset{\|}{C}} -,$$

$$\text{aryl} - (CH_2)_m - \overset{O}{\underset{\|}{C}} -, \text{ alkyl} - \overset{O}{\underset{\|}{C}} - O - \text{ or aryl} - (CH_2)_m - \overset{O}{\underset{\|}{C}} - O -;$$

amino or substituted amino;
m is 0 or an integer of 1 to 6;
n is an integer of 1 to 6; and
p is an integer of 2 to 6.

5 Claims, No Drawings

2-OXO-1-SULFONYL PYRAZOLO(1,5-A) PYRIMIDINE-6-CARBOXYLIC ACID ESTERS

BRIEF DESCRIPTION OF THE INVENTION

Compounds having the formula

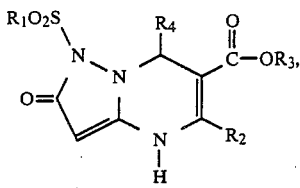

and pharmaceutically acceptable salts thereof, are cardivascular agents. In formula I, and throughtout the specification, the symbols are as defined below.

$R_1$ is alkyl, cycloalkyl, aryl, —$(CH_2)_n$—$Y_1$, or halo substituted alkyl;

$R_2$ is hydrogen, alkyl, alkenyl, alkynyl, cycloalkyl, aryl, —$(CH_2)_n$—$Y_1$, or halo substituted alkyl;

$R_3$ is hydrogen, alkyl, cycloalkyl, aryl, —$(CH_2)_n$—$Y_2$, —$(CH_2)_p$—$Y_3$, or halo substituted alkyl;

$R_4$ is aryl;

$Y_1$ is cycloalkyl, aryl, hydroxyl, alkoxy, aryl—$(CH_2)_m$—O—, mercapto, alkylthio, aryl—$(CH_2)_m$—S—, amino, substituted amino, carbamoyl,

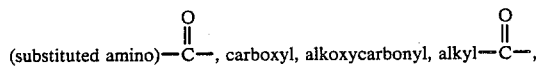

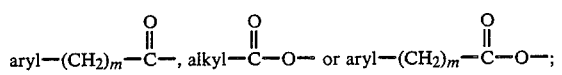

$Y_2$ is cycloalkyl, aryl, carbamoyl,

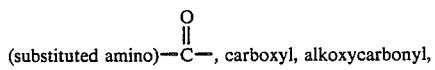

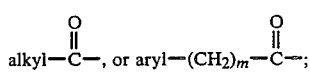

$Y_3$ is hydroxyl, alkoxy, aryl—$(CH_2)_m$—O—, mercapto, alkylthio, aryl—$(CH_2)_m$—S—,

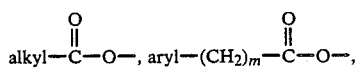

amino or substituted amino, m is 0 or an integer of 1 to 6;
n is an integer of 1 to 6; and
p is an integer of 2 to 6.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, which is preferred, pentafluoroethyl, 2,2,2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro cyano, trifluoromethyl, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "substituted amino" refers to a group of the formula —$NZ_1Z_2$ wherein $Z_1$ is hydrogen, alkyl, or aryl—$(CH_2)_m$— and $Z_2$ is alkyl or aryl—$(CH_2)_m$—or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

DETAILED DESCRIPTION OF THE INVENTION

The compounds of formula I, and the pharmaceutically acceptable salts thereof, are cardiovascular agents. They act as calcium entry blocking vasodilators and are especially useful as hypotensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, it is believed that such compounds in addition to being hypotensive agents may also be useful as anti-arrhythmic agents, anti-anginal agents, anti-fibrillatory agents, anti-asthmatic agents, anti-ischemic agents and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

To prepare the compounds of formula I, a compound of the formula

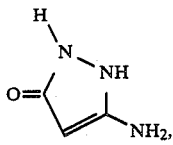
II that is, 3-amino-5-pyrazolone, is reacted with a keto ester having the formula

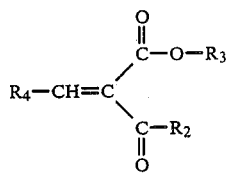
III to provide a compound of the formula

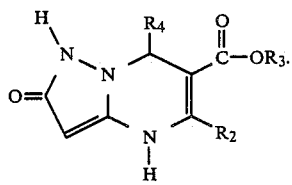
IV

The reaction is preferably heated in the presence of an organic solvent, such as dimethylformamide.

Compound IV in solvents, such as dicishloromethane and pyridine, is treated with a compound of the formula $R_1O_2S-Cl$     V to provide the compounds of formula I.

The compounds of formula I that contain a basic or acid group form acid addition and basic salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g. sodium, potassium and lithium) and alkaline earth metal salts (e.g. calcium and magnesium). The salts can be obtained by reacting the product with an equivalent amount of the acid in a medium in which the salt precipitates.

Preferred compounds of this invention are those wherein:

$R_1$ is aryl, $R_2$ is alkyl (especially methyl), $R_3$ is alkyl and $R_4$ is substituted phenyl (especially 3-nitrophenyl).

The following example are specific embodiments of this invention.

Example 1

1,2,4,7-Tetrahydro-5-methyl-7-(3-nitro-phenyl)-2-oxo-1-(phenylsulfonyl)pyrazolo-[1,5-a]pyrimidine-6-carboxylic acid, 1-methylethyl ester A.
1,2,4,7-Tetrahydro-5-methyl-7-(3-nitro-phenyl)-2-oxopyrazolo[1,5,-a]pyrimidine-6carboxylic acid, 1-methylethyl ester A mixture of 3-amino-5-pyrazolone (3.57 g, 36.1 mmole) and 2-[(3-nitrophenyl)methylene]-3-oxobutanoic acid, 1-methylethyl ester (10 g, 36.1 mmole) in dry dimethylformamide (30 ml) was heated at 70° C. under argon for 24 hours. The reaction mixture was allowed to cool to room temperature and then diluted with ether. The resultant precipitate was filtered off and recrystallized from isopropanol to provide 4.23 g of the title A compound in crystalline form, m.p. 254°-256° C.

Analysis calc'd for $C_{17}H_{18}N_4O_5$: C, 56.98; H, 5.06; N, 15.63;

Found: C, 57.18; H, 5.10; N, 15.70.

B.
1,2,4,7-Tetrahydro-5-methyl-7-(3-nitro-phenyl)-2-oxo-1-(phenylsulfonyl)pyrazolo-[1,5-a]pyrimidine-6-carboxylic acid, 1-methylethyl ester The suspension of the title A compound (1.07 g, 3.0 mmol) in dichloromethane (10 mL) and pyridine (2 mL) was treated at 0° C. under argon with benzenesulfonyl chloride (0.4 mL, 3.0 mmol). After the addition was finished, the cooling bath was removed and the reaction was allowed to stir at room temperature for 3 hours. The resulting solution was diluted with dichloromethane and was washed with 1N hydrochloric acid, water and brine. After drying over anhydrous magnesium sulfate, the solvent was removed and the residue was crystallized from ether-hexanes to yield 1.06 g of the title compound as a light yellow solid, m.p. 187°-188° C.

Analysis calc'd for $C_{23}H_{22}N_4O_7S$: C, 55.41; H, 4.45; N, 11.23; S, 6.43;

Found: C, 55.22; H, 4.38; N, 10.83; S, 6.62.

EXAMPLES 2-17

Using the procedures outlined above, the following additional compounds of formula I within the scope of the present invention can be made.

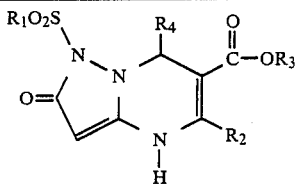

| Ex. No. | $R_1$ | $R_2$ | $R_3$ | $R_4$ |
|---|---|---|---|---|
| 2 | $CH_3$ | $CH_3$ | $CH_2CH_3$ | 2-Cl-C₆H₄ |
| 3 | $CH_2CH_3$ | $CH_3$ | $CH_2CH_3$ | 2,3-di-Cl-C₆H₃ |
| 4 | C₆H₅ | $CH_2$-C₆H₅ | $CH_3$ | 2-NO₂-C₆H₄ |
| 5 | $CH_3CH_2CH_2$ | $CH_2CH_3$ | $CH_2CH_2N(CH_3)CH_2$-C₆H₅ | 2-CF₃-C₆H₄ |
| 6 | $Cl-CH_2CH_3CH_2$ | $CH_3$ | $CH(CH_3)_2$ | 3-Cl-C₆H₄ |
| 7 | $CH_3CH_2$ | $CH_3$ | $CH_2CH_2$-N(piperidine) | 3-Br-C₆H₄ |
| 8 | $CH_3$ | $CH_2CH_2$-C₆H₅ | $CH_2CH_2OCH_2$-C₆H₅ | 3-Br-C₆H₄ |
| 9 | C₆H₅ | $CH_3$ | $CH_2CH_2OCH_3$ | 3-CN-C₆H₄ |
| 10 | C₆H₅-$CH_2N(CH_3)CH_2CH_2$ | $CH_3$ | $CH(CH_3)_2$ | 3-NO₂-C₆H₄ |
| 11 | thiomorpholine-N-$CH_2CH_2CH_2$ | $CH_3$ | $CH_2CH_3$ | 2-CF₃-C₆H₄ |

-continued

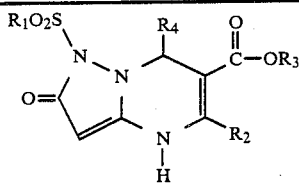

| Ex. No. | R₁ | R₂ | R₃ | R₄ |
|---|---|---|---|---|
| 12 | $CH_3CH_2$ | $CH_2CH_2NCH_2$-phenyl, with N-$CH_3$ | $CH_2CH_3$ | 2-Cl-phenyl |
| 13 | 4-Cl-phenyl | $CH_3$ | $CH(CH_3)_2$ | 3-$NO_2$-phenyl |
| 14 | 4-$CH_3$-phenyl | $CH_3$ | $CH_2CH_3$ | 2,3-diCl-phenyl |
| 15 | $CH_3$ | $CH_2CH_2N(CH_3)_2$ | $CH(CH_3)_2$ | 3-$NO_2$-phenyl |
| 16 | $(CH_3)_2CH$- | $CH_3$ | $CH_2CH_2N(CH_3)_2$ | 2-CN-phenyl |
| 17 | $CH_3CH_2$ | $CH_2CH_2OCH_3$ | $CH_2CH_3$ | 2-$OCHF_2$-phenyl |

What is claimed is:
1. A compound having the formula

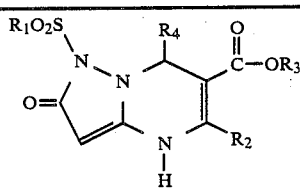

| Ex. No. | R₁ | R₂ | R₃ | R₄ |
|---|---|---|---|---|
| 2 | $CH_3$ | $CH_3$ | $CH_2CH_3$ | 2-Cl-phenyl |
| 3 | $CH_2CH_3$ | $CH_3$ | $CH_2CH_3$ | 2,3-diCl-phenyl |

-continued

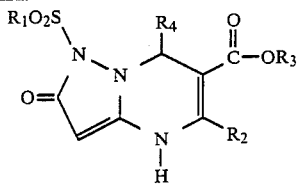

| Ex. No. | R₁ | R₂ | R₃ | R₄ |
|---|---|---|---|---|
| 4 | phenyl | $CH_2$–phenyl | $CH_3$ | 2-$NO_2$-phenyl |
| 5 | $CH_3CH_2CH_2$ | $CH_2CH_3$ | $CH_2CH_2N(CH_3)$–phenyl | 2-$CF_3$-phenyl |
| 6 | $Cl-CH_2CH_2CH_2$ | $CH_3$ | $CH(CH_3)_2$ | 3-Cl-phenyl |
| 7 | $CH_3CH_2$ | $CH_3$ | $CH_2CH_2$–N-piperidinyl | 3-Br-phenyl |
| 8 | $CH_3$ | $CH_2CH_2$–phenyl | $CH_2CH_2OCH_2$–phenyl | 3-Br-phenyl |
| 9 | phenyl | $CH_3$ | $CH_2CH_2OCH_3$ | 3-CN-phenyl |
| 10 | phenyl–$CH_2N(CH_3)$–$CH_2CH_2CH_2$ | $CH_3$ | $CH(CH_3)_2$ | 3-$NO_2$-phenyl |
| 11 | thiomorpholino-$N-CH_2CH_2CH_2$ | $CH_3$ | $CH_2CH_3$ | 2-$CF_3$-phenyl |
| 12 | $CH_3CH_2$ | $CH_2CH_2N(CH_3)CH_2$–phenyl | $CH_2CH_3$ | 2-Cl-phenyl |
| 13 | 4-Cl-phenyl | $CH_3$ | $CH(CH_3)_2$ | 3-$NO_2$-phenyl |

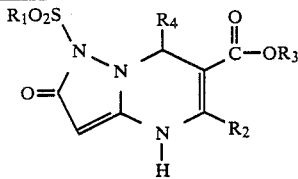

| Ex. No. | R₁ | R₂ | R₃ | R₄ |
|---|---|---|---|---|
| 14 | $CH_3$–C₆H₄– (p-tolyl) | $CH_3$ | $CH_2CH_3$ | 2,3-dichlorophenyl |
| 15 | $CH_3$ | $CH_2CH_2N(CH_3)_2$ | $CH(CH_3)_2$ | 3-nitrophenyl |
| 16 | $(CH_3)_2CH-$ | $CH_3$ | $CH_2CH_2N(CH_3)_2$ | 2-cyanophenyl |
| 17 | $CH_3CH_2$ | $CH_2CH_2OCH_3$ | $CH_2CH_3$ | 2-($OCHF_2$)phenyl | or a pharmaceutically acceptable salt thereof wherein
  $R_1$ is alkyl, cycloalkyl, aryl, $-(CH_2)_n-Y_1$, or halo substituted alkyl;
  $R_2$ is hydrogen, alkyl, alkenyl, alkynyl, cycloalkyl, aryl, $-(CH_2)_n-Y_1$, or halo substituted alkyl;
  $R_3$ is hydrogen, alkyl, cycloalkyl, aryl, $-(CH_2)_n-Y_2$, $-(CH_2)_p-Y_3$, or halo substituted alkyl;
  $R_4$ is aryl;
  $Y_1$ is cycloalkyl, aryl, hydroxyl, alkoxy, aryl$-(CH_2)_m-O-$, mercapto, alkylthio, aryl$-(CH_2)_m-S-$, amino, substituted amino, carbamoyl, (substituted amino)$-\overset{O}{\underset{\|}{C}}-$, carboxyl, alkoxycarbonyl, alkyl$-\overset{O}{\underset{\|}{C}}-$, aryl$-(CH_2)_m-\overset{O}{\underset{\|}{C}}-$, alkyl$-\overset{O}{\underset{\|}{C}}-O-$ or aryl$-(CH_2)_m-\overset{O}{\underset{\|}{C}}-O-$;

$Y_2$ is cycloalkyl, aryl, carbamoyl, (substituted amino)$-\overset{O}{\underset{\|}{C}}-$, carboxyl, alkoxycarbonyl, alkyl$-\overset{O}{\underset{\|}{C}}-$, or aryl$-(CH_2)_m-\overset{O}{\underset{\|}{C}}-$;

$Y_3$ is hydroxyl, alkoxy, aryl$-(CH_2)_m-O-$, mercapto, alkylthio aryl$-(CH_2)_m-S-$, alkyl$-\overset{O}{\underset{\|}{C}}-O-$, aryl$-(CH_2)_m-\overset{O}{\underset{\|}{C}}-O-$, amino or substituted amino;
  m is 0 or an integer of 1 to 6;
  n is an integer of 1 to 6; and
  p is an integer of 2 to 6;
wherein the terms "alkyl" and "alkoxy" refer to both straight and branched chain groups having 1 to 8 carbon atoms;
  the term "halo substituted alkyl" refers to alkyl groups in which one or more hydrogens have been replaced by chloro, bromo or fluoro groups;
  the term "aryl" refers to phenyl and substituted phenyl wherein the substituents are 1,2 or 3 groups independently selected from alkyl, alkoxy, alkylthio, halo, nitro cyano, trifluoromethyl, and difluoromethoxy;
  the terms "alkenyl" and "alkynyl" refer to both straight and branched chain groups having 2 to 8 carbon atoms;
  the term "cycloalkyl" refers to those groups having 3, 4, 5, 6 or 7 carbon atoms;
  the term "halo" refers to chloro, bromo, fluoro and iodo;
  the term "substituted amino" refers to a group of the formula $-NZ_1Z_2$ wherein $Z_1$ is hydrogen, alkyl, or aryl$-(CH_2)_m-$ and $Z_2$ is alkyl or aryl$-(CH_2)_m-$ or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

2. A compound in accordance with claim 1 wherein $R_1$ is aryl;

R$_2$ is alkyl;
R$_3$ is alkyl; and,
R$_4$ is substituted phenyl.

3. A compound in accordance with claim 1 wherein
R$_1$ is phenyl;
R$_2$ is methyl;
R$_3$ is isopropyl; and,
R$_4$ is 3-nitrophenyl.

4. A compound in accordance with claim 1 having the name 1,2,4,7-tetrahydro-5-methyl-7-(3-nitrophenyl)-2-oxo-1-(phenylsulfonyl)pyrazolo-[1,5-a]-pyrimidine-6-carboxylic acid, 1-methylethyl ester.

5. A method for reducing the blood pressure of a mammalian host in need thereof which comprises administering to said host an effective amount of a compound having the formula

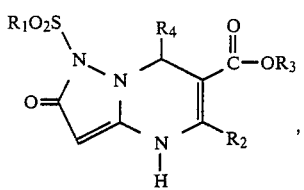

or a pharmaceutically acceptable salt thereof wherein
R$_1$ is alkyl, cycloalkyl, aryl, —(CH$_2$)$_n$—Y, or halo substituted alkyl;
R$_2$ is hydrogen, alkyl, alkenyl, alkynyl, cycloalkyl, aryl, —(CH$_2$)$_n$—Y$_1$, or halo substituted alkyl;
R$_3$ is hydrogen, alkyl, cycloalkyl, aryl, —(CH$_2$)$_n$—Y$_2$, —(CH$_2$)$_p$—Y$_3$, or halo substituted alkyl;
R$_4$ is aryl;
Y$_1$ is cycloalkyl, aryl, hydroxyl, alkoxy, aryl—(CH$_2$)$_m$—O—, mercapto, alkylthio, aryl—(CH$_2$)$_m$—S—, amino, substituted amino, carbamoyl, $$\text{(substituted amino)}-\overset{\overset{O}{\|}}{C}-,\ \text{carboxyl, alkoxycarbonyl, alkyl}-\overset{\overset{O}{\|}}{C}-,$$

$$\text{aryl}-(CH_2)_m-\overset{\overset{O}{\|}}{C}-,\ \text{alkyl}-\overset{\overset{O}{\|}}{C}-O-\ \text{or aryl}-(CH_2)_m-\overset{\overset{O}{\|}}{C}-O-;$$

Y$_2$ is cycloalkyl, aryl, carbamoyl, $$\text{(substituted amino)}-\overset{\overset{O}{\|}}{C}-,\ \text{carboxyl, alkoxycarbonyl,}$$

$$\text{alkyl}-\overset{\overset{O}{\|}}{C}-,\ \text{or aryl}-(CH_2)_m-\overset{\overset{O}{\|}}{C}-;$$

Y$_3$ is hydroxyl, alkoxy, aryl—(CH$_2$)$_m$—O—, mercapto, alkylthio, aryl—(CH$_2$)$_m$—S—, $$\text{alkyl}-\overset{\overset{O}{\|}}{C}-O-,\ \text{aryl}-(CH_2)_m-\overset{\overset{O}{\|}}{C}-O-,$$

m is 0 or an integer of 1 to 6;
n is an integer of 1 to 6; and
p is an integer of 2 to 6.

* * * * *